US010981152B2

(12) United States Patent
Canos et al.

(10) Patent No.: US 10,981,152 B2
(45) Date of Patent: Apr. 20, 2021

(54) MESOPOROUS ZSM-22 FOR INCREASED PROPYLENE PRODUCTION

(71) Applicant: Albemarle Corporation, Charlotte, NC (US)

(72) Inventors: Avelino Corma Canos, Valencia (ES); Joaquin Martinez-Triguero, Manises (ES)

(73) Assignee: ALBEMARLE CORPORATION, Charlotte, NC (US)

( * ) Notice: Subject to any disclaimer, the term of this patent is extended or adjusted under 35 U.S.C. 154(b) by 0 days.

(21) Appl. No.: 16/311,783

(22) PCT Filed: Jun. 24, 2017

(86) PCT No.: PCT/US2017/039158
§ 371 (c)(1),
(2) Date: Dec. 20, 2018

(87) PCT Pub. No.: WO2017/223546
PCT Pub. Date: Dec. 28, 2017

(65) Prior Publication Data
US 2019/0168196 A1    Jun. 6, 2019

Related U.S. Application Data

(60) Provisional application No. 62/354,451, filed on Jun. 24, 2016.

(51) Int. Cl.
*B01J 29/70*    (2006.01)
*B01J 29/40*    (2006.01)
(Continued)

(52) U.S. Cl.
CPC .......... *B01J 29/7042* (2013.01); *B01J 29/40* (2013.01); *B01J 29/80* (2013.01); *B01J 35/1019* (2013.01);
(Continued)

(58) Field of Classification Search
CPC .... B01J 29/7042; B01J 37/06; B01J 35/1038; B01J 35/1019; B01J 29/80; B01J 29/40;
(Continued)

(56) References Cited

U.S. PATENT DOCUMENTS 3,758,403 A    9/1973  Rosinski et al.
3,769,202 A    10/1973 Plank et al.
(Continued)

FOREIGN PATENT DOCUMENTS

CN    101619011 A    1/2010
CN    102191081 A    9/2011
(Continued)

OTHER PUBLICATIONS

Verboekend et al. ("Mesoporous ZSM-22 zeolite obtained by desilication: peculiarities associated with crystal morphology and aluminium distribution", CrystEngComm, 2011, 13, 3408 (Year: 2011).*
(Continued)

*Primary Examiner* — Ali Z Fadhel
(74) *Attorney, Agent, or Firm* — Nathaniel C. Dunn; Marcy M. Hoefling; Troy S. Kleckley

(57) ABSTRACT

The present invention pertains to the use of mesoporous ZSM-22 zeolite in a process for the cracking or conversion of a feed comprised of hydrocarbons, such as, for example, that obtained from the processing of crude petroleum, to a mixture high in propylene. Further, the present invention concerns the field of fluid catalytic cracking (FCC) processes and relates to the preparation and employment of additives based on zeolites having increased mesoporosity, such as altered ZSM-22. More particularly the present invention discloses a process for improving the production of propylene in FCC units.

6 Claims, 2 Drawing Sheets propylene and aromatic selectivity plots for 0.3 g meso-ZSM-22 and 1 g of commercial ZSM-5 for the cracking of C5-C6-C7 olefins at 520°C and 30 sec TOS.

(51) Int. Cl.

| | | |
|---|---|---|
| B01J 29/80 | (2006.01) | |
| B01J 35/10 | (2006.01) | |
| B01J 37/06 | (2006.01) | |
| C01B 39/38 | (2006.01) | |
| C07C 4/06 | (2006.01) | |

(52) U.S. Cl.
CPC ............ *B01J 35/1038* (2013.01); *B01J 37/06* (2013.01); *C01B 39/38* (2013.01); *C07C 4/06* (2013.01); *B01J 2229/12* (2013.01); *B01J 2229/38* (2013.01); *C07C 2529/40* (2013.01); *C07C 2529/70* (2013.01)

(58) Field of Classification Search
CPC ..... B01J 2229/38; B01J 2229/12; C07C 4/06; C07C 2529/70; C07C 2529/40; C01B 39/38

See application file for complete search history.

(56) References Cited

U.S. PATENT DOCUMENTS

| | | |
|---|---|---|
| 3,894,931 A | 7/1975 | Nace et al. |
| 3,894,933 A | 7/1975 | Owen et al. |
| 3,894,934 A | 7/1975 | Owen et al. |
| 3,926,782 A | 12/1975 | Plank et al. |
| 4,309,279 A | 1/1982 | Chester et al. |
| 4,309,280 A | 1/1982 | Rosinski et al. |
| 4,375,458 A | 3/1983 | Dwyer et al. |
| 4,481,177 A | 11/1984 | Valyocsik |
| 4,483,835 A | 11/1984 | Zones |
| 4,900,528 A | 2/1990 | Lowe et al. |
| 4,902,406 A | 2/1990 | Valyocsik |
| 4,973,399 A | 11/1990 | Green et al. |
| 5,006,497 A | 4/1991 | Herbst et al. |
| 5,179,054 A * | 1/1993 | Schipper ................. B01J 33/00 502/65 |
| 5,294,332 A | 3/1994 | Klotz |
| 5,321,194 A | 6/1994 | Apelian et al. |
| 5,342,596 A | 8/1994 | Barri et al. |
| 5,456,821 A | 10/1995 | Absil et al. |
| 5,521,133 A | 5/1996 | Koermer et al. |
| 5,866,096 A | 2/1999 | Verduijn et al. |
| 6,143,942 A | 11/2000 | Verrelst et al. |
| 6,656,345 B1 | 12/2003 | Chen et al. |
| 6,867,341 B1 | 3/2005 | Abrevaya et al. |
| 7,094,390 B2 | 8/2006 | Sterte et al. |
| 7,267,759 B2 | 9/2007 | Chen et al. |
| 7,270,739 B2 | 9/2007 | Chen et al. |
| 7,304,011 B2 | 12/2007 | Yaluris et al. |
| 7,314,964 B2 | 1/2008 | Abrevaya et al. |
| 7,326,332 B2 | 2/2008 | Chen et al. |
| 7,446,071 B2 | 11/2008 | Abrevaya et al. |
| 7,585,489 B2 | 9/2009 | Abrevaya et al. |
| 7,641,787 B2 | 1/2010 | Yaluris et al. |
| 7,960,597 B2 | 6/2011 | Miller |
| 8,137,533 B2 | 3/2012 | Towler et al. |
| 2002/0192155 A1 | 12/2002 | Sterte et al. |
| 2004/0029716 A1 | 2/2004 | Mohr et al. |
| 2004/0182745 A1 | 9/2004 | Chen et al. |
| 2004/0182746 A1 | 9/2004 | Chen et al. |
| 2005/0070422 A1* | 3/2005 | Chen ..................... B01J 29/005 502/64 |
| 2005/0075526 A1 | 4/2005 | Abrevaya et al. |
| 2005/0100493 A1 | 5/2005 | Yaluris et al. |
| 2005/0130832 A1 | 6/2005 | Abrevaya et al. |
| 2005/0230285 A1 | 10/2005 | Yaluris et al. |
| 2008/0213150 A1 | 9/2008 | Yaluris et al. |
| 2008/0318764 A1 | 12/2008 | Abrevaya et al. |
| 2009/0050527 A1 | 2/2009 | Krishnamoorthy et al. |
| 2009/0068079 A1 | 3/2009 | Yaluris et al. |
| 2009/0124842 A1 | 5/2009 | Reagan et al. |
| 2010/0105974 A1 | 4/2010 | Towler et al. |
| 2014/0357912 A1* | 12/2014 | Mandal ..................... C07C 4/06 585/302 |
| 2018/0002612 A1* | 1/2018 | Kumar .................... C10G 51/02 |

FOREIGN PATENT DOCUMENTS

| | | |
|---|---|---|
| CN | 102690683 A | 9/2012 |
| EP | 0087017 A1 | 8/1983 |
| JP | 2004105859 A | 4/2004 |
| JP | 2006519256 A | 8/2006 |
| JP | 2006520845 A | 9/2006 |
| JP | 4227790 B2 | 2/2009 |
| JP | 4524280 B2 | 8/2010 |
| JP | 4747089 B2 | 8/2011 |
| WO | 1994013754 A1 | 6/1994 |
| WO | 1999057226 A1 | 11/1999 |
| WO | 2004078882 A1 | 9/2004 |
| WO | 2004078883 A1 | 9/2004 |
| WO | 2005035118 A1 | 4/2005 |
| WO | 2008014920 A2 | 2/2008 |
| WO | 2008147190 A1 | 12/2008 |

OTHER PUBLICATIONS

Koyama et al., "Key role of the pore volume of zeolite for selective production of propylene from olefins", Phys. Chem. Chem. Phys., 2010, 12, 2541-2554 | 2541 (Year: 2010).*

Kokotailo, G.T., et al., "The Framework Topology of ZSM-22: A High Silica Zeolite," Zeolites, Nov. 1985, pp. 349-351, vol. 5, all enclosed pages cited.

Madon, R. J., "Role of ZSM-5 and Ultrastable Y Zeolites for Increasing Gasoline Octane Number," Journal of Catalysis, 1991, pp. 275-287, vol. 129, all enclosed pages cited.

Martens, J.A., et al., Selective Conversion of Decane into Branched Isomers: A Comparison of Platinum/ZSM-22, Platinum/ZSM-5, USY Zeolite Catalysts, Applied Catalysis, 1991, pp. 95-116, vol. 76, all enclosed pages cited.

Dwyer, F.G., et al., "Fluid Catalytic Cracking: Science and Technology, Shape Selectivity in Catalytic Cracking," Studies in Surface Science and Catalysis, 1993, vol. 76, Ch. 13, pp. 499-530, Elsevier Science Publishers B.V., all enclosed pages cited.

Mordi, R.C., et al., "Thermolysis of Low Density Polyethylene Catalysed by Zeolites," Journal of Analytical and Applied Pyrolysis, 1994, pp. 45-55, vol. 29, all enclosed pages cited.

Buchanan, J.S., et al., "Effects of High Temperature and High ZSM-5 Additive Level on FCC Olefins Yields and Gasoline Composition," Applied Catalysis A: General, 1996, pp. 247-262, vol. 134, all enclosed pages cited.

Souverijns, W., et al., "Hydrocracking of Isoheptadecanes on Pt/H-ZSM-22: An Example of Pore Mouth Catalysis," Journal of Catalysis, 1998, pp. 177-184, vol. 174, Art. CA971959, all enclosed pages cited.

Claude, M.C., et al., "Monomethyl-Branching of Long n-Alkanes in the Range from Decane to Tetracosane on Pt/H-ZSM-22 Bifunctional Catalyst," Journal of Catalysis, 2000, pp. 39-48, vol. 190, all enclosed pages cited.

Park, K.C., et al., "Comparison of Pt/Zeolite Catalysts for n-Hexadecane Hyrdoisomerization," Applied Catalysis A: General, 2000, pp. 201-209, vol. 203, all enclosed pages cited.

Claude, M.C., et al., "Dimethyl Branching of Long n-Alkanes in the Range from Decane to Tetracosane on Pt/H-ZSM-22 Bifunctional Catalyst," Journal of Catalysis, 2001, pp. 213-231, vol. 203, all enclosed pages cited.

Groen, J.C., et al., "On the Introduction of Intracrystalline Mesoporosity in Zeolites Upon Desilication in Alkaline Medium," Microporous and Mesoporous Materials, 2004, pp. 29-34, vol. 69, all enclosed pages cited.

Deldari, H., "Suitable Catalysis for Hydroisomerization of Long-Chain Normal Paraffins," Applied Catalysis A: General, 2005, pp. 1-10, vol. 293, all enclosed pages cited.

Stöcker, M., "Gas Phase Catalysis by Zeolites," Microporous and Mesoporous Materials, 2005, pp. 257-292, vol. 82, all enclosed pages cited.

Hancsók, J., et al., "Investigation of the Production of High Cetane Number Bio Gas Oil from Pre-Hydrogenated Vegetable Oils Over Pt/HZSM-22/Al2O3," Microporous and Mesoporous Materials, 2007, pp. 148-152, vol. 101, all inclosed pages cited.

(56) References Cited

OTHER PUBLICATIONS

Masih, D., et al., "Hydrothermal Synthesis of Pure ZSM-22 Under Mild Conditions," Chem. Comm., The Royal Society of Chemistry, 2007, pp. 3303-3305, all enclosed pages cited.

Pérez-Ramírez, J., et al., "Hierarchical Zeolites: Enhanced Utilisation of Microporous Crystals in Catalysis by Advances in Materials Design," Chemical Society Reviews, The Royal Society of Chemistry, 2008, pp. 2530-2542, vol. 37, all enclosed pages cited.

Bonilla, A., et al., "Desilication of Ferrierite Zeolite for Porosity Generation and Improved Effectiveness in Polyethylene Pyrolysis," Journal of Catalysis, 2009, pp. 170-180, vol. 265, all enclosed pages cited.

Fernandez, C., et al., "Hierarchical ZSM-5 Zeolites in Shape-Selective Xylene Isomerization: Role of Mesoporosity and Acid Site Speciation," Chemistry: A European Journal, 2010, pp. 6244-6233, vol. 16, all enclosed pages cited.

Bager, F., et al., "The Potential of Medium-Pore Zeolites for Improved Propene Yields from Catalytic Cracking," Catalysis—Innovative Applications in Petrochemistry and Refining, DGMK Conference, Oct. 4-6, 2011, Dresden, Germany, pp. 127-134, all enclosed pages cited.

Verboekend, D., et al., "Mesoporous ZSM-22 Zeolite Obtained by Desilication: Peculiarities Associated with Crystal Morphology and Aluminum Distribution," CrystEngComm, 2011, pp. 3408-3416, vol. 13, all enclosed pages cited.

Verboekend, D., et al., "Full Compositional Flexibility in the Preparation of Mesoporous MFI Zeolites by Desilication," The Journal of Physical Chemistry, 2011, pp. 14193-14203, vol. 115, all enclosed pages cited.

Verboekend, D., et al., "Towards More Efficient Monodimensional Zeolite Catalysts: n-Alkane Hydro-Isomerisation of Hierarchical ZSM-22," Catalyis Science & Technology, 2011, pp. 1331-1335, vol. 1, all enclosed pages cited.

Bager, F., et al., "Improved Propene Yields from Catalytic Cracking: The Potential of Medium-Pore Zeolites as Additives," Oil Gas European Magazine, Petrochemistry, 2012, pp. 107-111, vol. 2, all enclosed pages cited.

International Search Report and Written Opinion of corresponding international application No. PCT/US2017/039158 dated Sep. 27, 2019, all enclosed pages cited.

International Preliminary Report on Patentability of corresponding international application No. PCT/US2017/039158 dated Dec. 25, 2018, all enclosed pages cited.

"Database of Zeolite Structures," http://www.iza-structure.org/databases/, Structure Commission of the International Zeolite Association, last accessed Mar. 6, 2019, all enclosed material cited.

Price, J.L., "TCU Chemical Engineering Zeolite Page" http://www.personal.utulsa.edu/~geoffrey-price/zeolite/, last accessed Mar. 6, 2019, all enclosed material cited.

* cited by examiner

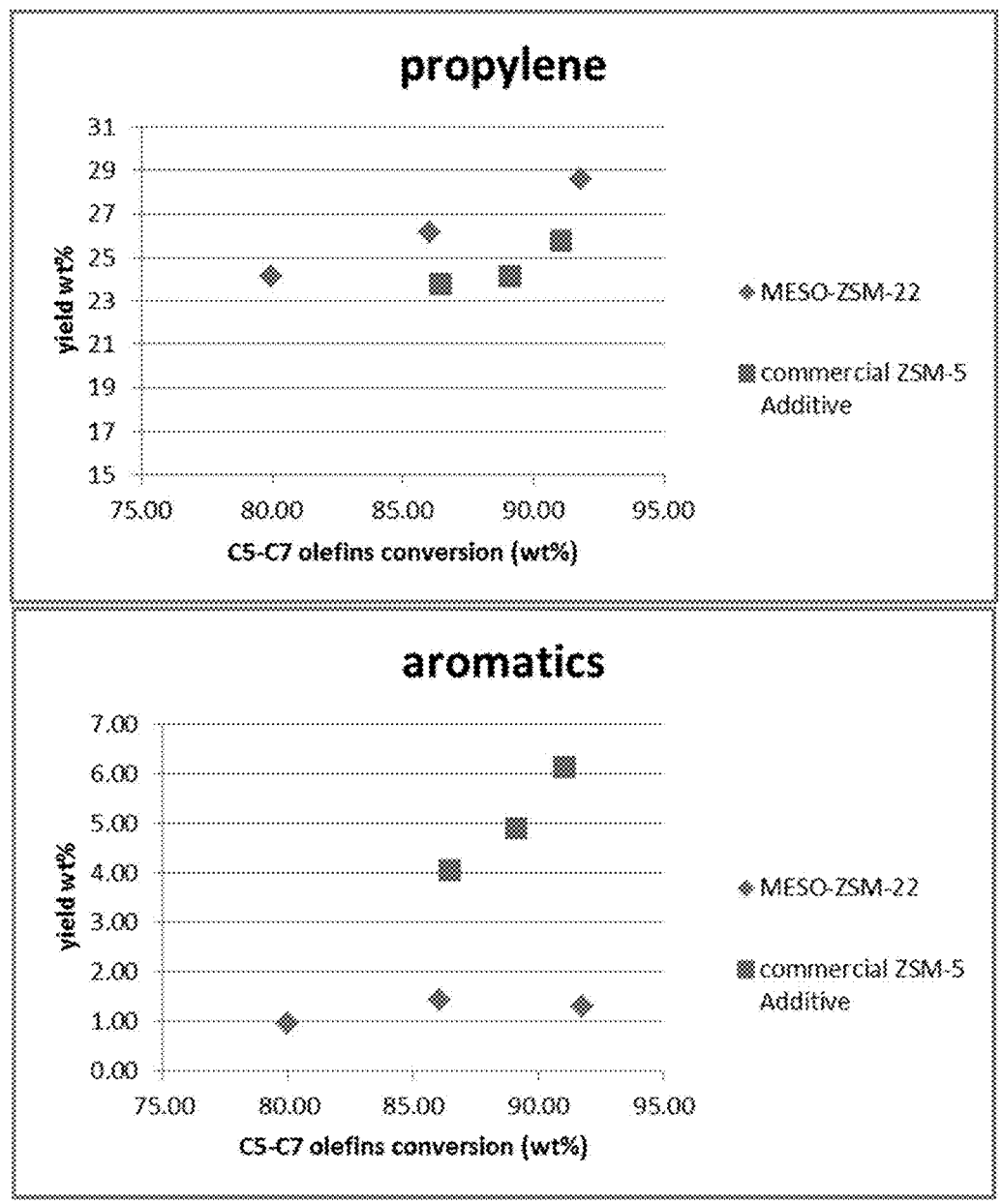
Figure 1. propylene and aromatic selectivity plots for 0.3 g meso-ZSM-22 and 1 g of commercial ZSM-5 for the cracking of C5-C6-C7 olefins at 520°C and 30 sec TOS.

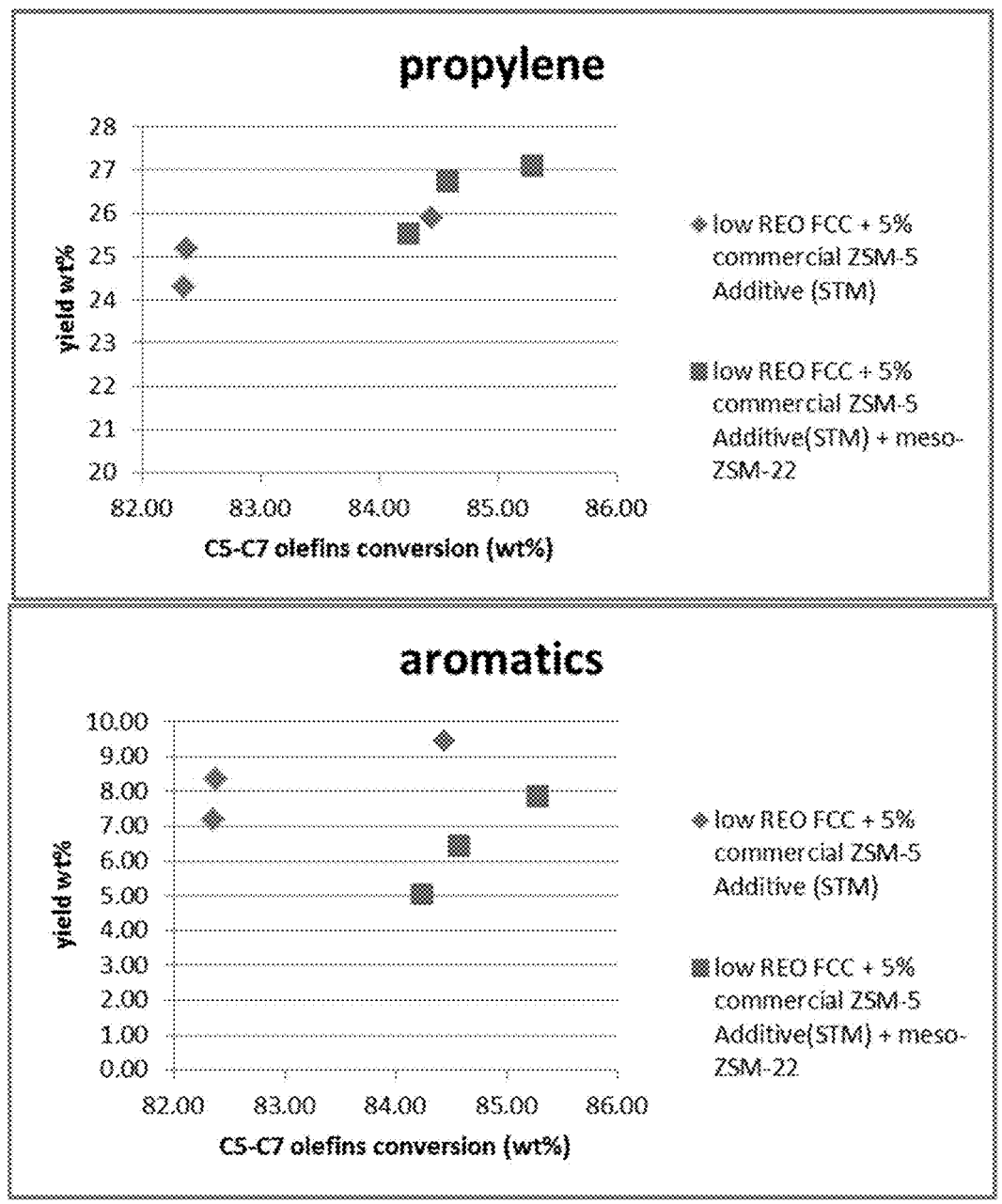
Figure 2. propylene and aromatic selectivity plots for FCC+ Commercial ZSM-5 and FCC+ Commercial ZSM-5+meso-ZSM-22 for the cracking of C5-C6-C7 olefins at 520°C and 30 sec TOS.

MESOPOROUS ZSM-22 FOR INCREASED PROPYLENE PRODUCTION

FIELD OF THE INVENTION

The present invention pertains to the use of mesoporous ZSM-22 zeolite in a process for the cracking or conversion of a feed comprised of hydrocarbons, such as, for example, that obtained from the processing of crude petroleum, to a mixture high in propylene. Further, the present invention concerns the field of fluid catalytic cracking (FCC) processes and relates to the preparation and employment of additives based on zeolites having increased mesoporosity, such as altered ZSM-22. More particularly the present invention discloses a process for improving the production of propylene in FCC units.

BACKGROUND INFORMATION

Fluid catalytic cracking (FCC) is carried out by contacting hydrocarbons in a tubular reaction zone or riser with a catalyst constituted by fine particulate material. Feedstocks most commonly subjected to the FCC process are, in general, streams from petroleum refineries from vacuum tower side cuts, denominated heavy vacuum gas oil (HVGO), or heavier streams from the bottom of atmospheric towers, denominated atmospheric residue (RAT), or mixtures of such streams. Said streams, having a density typically in the band from 8° API to 28° API, require subjection to a chemical process, such as the catalytic cracking process, fundamentally modifying the composition thereof, converting them into streams of lighter hydrocarbons having a greater economic value.

During the cracking reaction substantial quantities of coke, byproduct of the reactions, are deposited on the catalyst. Spent catalyst is directed to a regeneration zone wherein coke is burnt off the catalyst. Elimination of coke through combustion permits recovery of the activity of the catalyst and release of heat in sufficient quantity to provide the thermal requirements of the catalytic cracking reactions.

Since initial conception, the FCC process has essentially been directed to the production of high-octane petrol, being also responsible for LPG production. The middle distillate (LCO) produced is essentially aromatic, which fact renders the incorporation thereof into the diesel pool difficult. However, current and future scenarios indicate a fall in consumption of petrol and an increase in demand for diesel oil. Fluidic Catalytic Cracking units are playing an increasingly important role in the production of propylene.

In FCC practice, there are two ways to increase light olefin selectivity. The first of these is to increase the reaction temperature. This will increase the contribution of thermal cracking, which leads to increased formation of lighter products. For instance, in the so-called DCC (Deep Catalytic Cracking) process, a specific type of FCC process, higher temperatures and increased amounts of steam are used. However, thermal cracking is not very selective and produces large amounts of products of relatively little value, such as hydrogen, methane, ethane, and ethylene, in the "wet gas" (which contains H2 and C1-C4 products). Wet gas compression often limits refinery operation.

The second method is to add an olefin-selective, zeolite-containing additive such as a ZSM-5-containing additive. Conventional additives usually contain phosphorus-activated ZSM-5, which selectively converts primary cracking products (e.g., gasoline olefins) to C3 and C4 olefins. Improvement of the activity or the selectivity with phosphorus is known to increase the effectiveness of ZSM-5. For instance, EP-A-511 013 describes the treatment of ZSM-5 with phosphorus to increase the propylene selectivity. Further, U.S. Pat. No. 5,472,594 describes a process for converting a hydrocarbon feed to a product containing improved yields of C4/C5 olefins with a catalyst composition containing zeolite Y and an additive comprising a phosphorus-containing medium pore zeolite such as ZSM-5. Also Mobil's WO 98/41595 describes a process for the catalytic cracking of a hydrocarbon feedstock to produce an enhanced yield of C3 to C5 olefins using a catalyst composition comprising a large pore molecular sieve such as zeolite Y and an additive comprising a phosphorus-containing ZSM-5 blended in with the base catalyst containing zeolite Y. The same is described in U.S. Pat. No. 5,456,821. WO 94/13754 describes the same process using a catalyst composition containing a large pore molecular sieve and an additive containing a specific ZSM-5 which optionally contains 1.5 to 5.5 wt % elemental phosphorus. Also U.S. Pat. No. 5,521,133 describes the preparation of a ZSM-5 additive by injecting a ZSM-5 and kaolin slurry with phosphoric acid prior to spray-drying.

In EP 1445297 the use of zeolite ITQ-21, a three-dimensional large-pore zeolite with a very open structure which is more active in the conversion of a vacuum gasoil and propylene selectively to a commercial USY zeolite described ultra-stabilized is disclosed. In WO2008/014920 it is shown that the ITQ-33 zeolite having pores extra-large 18 MR (12.2 A) and 10 MR channels interconnected average pore simultaneously produces high yields diesel and light olefins, particularly propylene. However, the practical application of these new materials is limited due to its high manufacturing cost.

The production of propylene in the FCC can be increased by modifying the operating conditions of the unit, such as increasing the reactor temperature. However, this solution causes a considerable increase in gases and especially in undesired dry gas. The use of zeolite ZSM-5 as additive in FCC catalysts leads to an increase in olefins C3 and C4 (see for example U.S. Pat. Nos. 3,758,403, 3,769,202, 3,894,931, 3,894,933, 3,894,934; 3,926,782, 4,309,280, 4,309,279, 437,458 and Buchanan, J S and Adewuyi, Y G, Applied Catalysis: A General, 134, 247 (1996), Madon, R J, Journal of Catalysis 129 (1), 275 (1991).

Therefore, there remains a need to develop a novel catalyst additive that is selective to increase propylene production, produces low aromatics and is cost effective.

BRIEF DESCRIPTION OF THE INVENTION

The present invention describes a cracking process for organic compounds and, preferably, from petroleum fractions or synthetic hydrocarbons using a modified zeolite material, whose structure is characterized by the presence of additional mesoporosity. ZSM-22 is altered to give it mesoporosity. An optimum structure would present enough space to perform cracking reactions of olefins with no aromatization. It means a compromise between the ratio of mono to bimolecular cracking, and cracking to hydrogen transfer. The ZSM-22 with increased mesoporosity is then utilized as an additive in a FCC process.

These and still other embodiments, advantages and features of the present invention shall become further apparent from the following detailed description, including the appended claims.

BRIEF DESCRIPTION OF THE DRAWINGS

FIG. 1. propylene and aromatic selectivity plots for 0.3 g meso-ZSM-22 and 1 g of Commercial ZSM-5 for the cracking of C5-C6-C7 olefins at 520° C. and 30 sec TOS.

FIG. 2. propylene and aromatic selectivity plots for FCC+ Commercial ZSM-5 and FCC+ Commercial ZSM-5+meso-ZSM-22 for the cracking of C5-C6-C7 olefins at 520° C. and 30 sec TOS.

DETAILED DESCRIPTION OF THE INVENTION

Unless otherwise indicated, weight percent (wt %) as used herein is the weight percent of the specified form of the substance, based upon the total weight of the product for which the specified substance or form of substance is a constituent or component. It should further be understood that, when describing steps or components or elements as being preferred in some manner herein, they are preferred as of the initial date of this disclosure, and that such preference(s) could of course vary depending upon a given circumstance or future development in the art.

One of the most preferred methods to convert heavy hydrocarbon feed stocks to lighter products, such as gasoline and distillate range fractions is fluid catalytic cracking (FCC). There is, however, an increasing need to enhance the yield of lower olefins, LPG, propylene and other light olefin yields (C2-C4 hydrocarbon) in the product slate from catalytic cracking processes. The present invention relates to an additive specifically meant to be employed in the process for cracking, a hydrocarbon feed over a particular catalyst composition to produce conversion product hydrocarbon compounds of lower molecular weight than feed hydrocarbons, e.g., product comprising a high propylene fraction and increased LPG.

The present invention provides a fluid catalytic cracking (FCC) process for FCC units employing conditions of operation of low severity with a view to increasing production of LPG and light olefins and maximisation of middle distillates of low aromaticity, such that they may be incorporated into the diesel oil pool. The said process differs from processes found in the state of the art by virtue of employing an original catalytic system. The invention furthermore provides an additive for catalytic systems, the method of preparation thereof is disclosed below. Said catalyst is an FCC catalyst selective for light olefins, that is to say an FCC catalyst containing a zeolite selective for light olefins, such as zeolites of the ZSM-22 type.

The primary zeolite used in the present invention is typically ZSM-22. ZSM-22 is a zeolite of TON structure with a monodimmensional system of channels defined by 10 member rings with no cavities or crossings. ZSM-22 is typically used in amounts between about 5 wt % and 60 wt % on the dried basis.

It was found that when cracking olefins, propylene is maximized if aromatization and hydrogen transfer reactions are limited. In this way, the structure of monodimmensional 10 MR zeolites does not present space enough to allow bimolecular reactions as those producing aromatics and paraffins. However, monodimmensional 10 MR zeolites can present restrictional diffusion that result in lower activity compared with tridimensional 10 MR zeolites, such as ZSM-5. Due to the diffussional problems of monodimmensional structures, that decreases overall activity and consequently a larger amount of zeolite is needed for obtaining the desired activity. However, the increase of mesoporosity within the ZSM-22 can be utilized to overcome these deficiencies.

Mesoporosity can be obtained by different methods as known in the art. It can be obtained by synthesis procedures that decrease the size of the crystallites. In this case, the length of the channels is decreased allowing reactants and products to freely diffuse, decreasing secondary reactions. As an alternative to synthesis, the postsynthesis development of mesoporosity can be performed by NaOH treatment, as set forth in the art. For purposes of this invention, it is preferred that the treated ZSM-22 to have $V_{mesopore}$ ($cm^3/g$) of greater than about 0.075 $cm^3/g$ and more preferably greater than about 0.100 $cm^3/g$. Further, it is preferred that the treatment to create mesoporosity increases the $V_{mesopore}$ ($cm^3/g$) by at least about a factor of 1.5, and more preferred to increase the $V_{mesopore}$ ($cm^3/g$) by at least about a factor of 2.

Though from the catalytic point of view, the effect is very similar to a reduction in the size of the crystal by synthesis. The procedure of generation of mesoporosity also called "desilication," is done at aqueous basic conditions of pH and moderate temperatures. Silica is dissolved creating mesopores whose size is determined by Al content (that is not dissolved), temperature, time and the addition of additives. Subsequently, the excess of aluminum deposited as debris in the mesopores is removed by moderate acid treatment.

Desilication controlled in basic medium is described in the literature as an economical and effective process, which generates additional mesoporosity in zeolitic microporous structures (see Groen et al. Micro. Meso. Mater. 69 (2004) 29, Perez-Ramirez et al. Chem Soc Rev. 37 (2008) 2530). In WO2008/147190 preparing a mesoporous zeolite mordenite by a treatment which generates alkaline extraction silicon mesoporosity is described. The alkali treatment can be used independently or in combination with post-synthesis treatments. For example, performing sequentially basic and acid treatments can be effective for improving the catalytic performance of a zeolite material. The basic treatment creates mesopores, while the acid treatment dissolves the extra-network species, rich in aluminum, and modifies the surface acidity of the sample (see, for example, Fernandez et al., Chem Eur J 16 (2010) 6224, Verboekend et al. J. Phys Chem A 115 (2011) 14193, Catal. Technol. 1 (2011) 1331).

The ZSM-22 precursor material can be made as it is known in the art. For example as shown in U.S. Pat. No. 7,094,390. Typical ZSM-22 sample presents by SEM morphology of rods or needles of about 2 microns long but can be of a size known in the skill in the art. Si/Al ratios range from 25 to 75 and their acidity varies being higher for ZSM22-C, with the larger amount of Brönsted acidity measured by pyridine adsorption. The characterization of the ZSM-22 can be as follows:

| Sample | Si/Al | BET ($m^2/g$) | $V_{micropore}$ ($cm^3/g$) |
| --- | --- | --- | --- |
| ZSM22-A | 25 | 210 | 0.083 |
| ZSM22-B | 30 | 209 | 0.081 |
| ZSM22-C | 40 | 218 | 0.084 |

| | Acidity (absorbance units ×10³) | | | | | |
|---|---|---|---|---|---|---|
| Sample | B150 | B250 | B350 | L150 | L250 | L350 |
| ZSM22-A | 112 | 124 | 50 | 30 | 37 | 27 |
| ZSM22-B | 107 | 115 | 61 | 22 | 18 | 11 |
| ZSM22-C | 195 | 168 | 125 | 27 | 21 | 17 |

As one typical example, ZSM22-C was submitted to basic treatment with a solution 0.2M of NaOH in liquid to solid ratio of 33:1 at 65° C. for 30 min under stirring. After washing and filtering until pH=7, the solid was resuspended in a solution of oxalic acid (1 g zeolite 2.55 oxalic 25.5 g water) at 70° C. for 2 h with subsequent washing, filtering and calcinations at 375° C. 3 h. The sample was named mesoporous-ZSM-22. As shown in Table below, the mesopore volume was increased by a factor of two while microporosity is preserved, indicating that the crystalline structure has been also maintained. The final Si/Al ratio was very similar to the original sample. The volume of pores was measured using N2 adsorption, as is known in the art.

| Sample | ZSM-22-C | Mesoporous-ZSM-22 |
|---|---|---|
| Si/Al | 40 | 35 |
| BET (m²/g) | 218 | 241 |
| $V_{micropore}$ (cm³/g) | 0.084 | 0.083 |
| $V_{mesopore}$ (cm³/g) | 0.059 | 0.114 |

When the mesoporous sample was tested in the cracking of olefins, the mesoporous sample presented improved properties with higher yield to propylene. And, despite the similar conversion level obtained comparing with the parent sample, the distribution of olefins is closer to the thermodynamic equilibrium, with higher C3/C4 ratios and also higher yield to ethylene.

The results below show a higher yield of propylene obtained with ZSM-22 with increased mesoporosity than for ZSM-5. The higher amount of propylene comparing with ZSM-5 based catalyst is believed to be attributed to the reduced amount of aromatics formed in the monodimmensional channels of ZSM-22 that limits the bimolecular reactions leading to aromatics. In fact, the yield of aromatics obtained with ZSM-5 is twice or more the yield obtained with ZSM-22. In addition, the reduced isobutane and lower amount of isobutene on ZSM-22, which diffusion is more restricted than in ZSM-5, changes the thermodynamic distribution of C2-C6 olefins, with a higher ceiling for propylene.

From the results, zeolite ZSM-22 with increased mesoporosity displays good properties for increasing propylene. However, along with any increase in mesoporosity, one must be careful to not compromise hydrothermal stability. ZSM-22 should be added in a larger amount than ZSM-5, due to diffusion limitations. In other words, an optimum structure would present enough space to perform cracking reactions of olefins with no aromatization. It means a compromise between the ratio of mono to bimolecular cracking. If the space is restricted, cracking will be slower and monomolecular, and for pentenes will result to high yield to ethylene. On the other hand, if there is too much space, by crossing channels or cavities, cracking will also be bimolecular (oligomerization-cracking) and much faster, but cyclization, aromatization reactions and also hydrogen transfer will be lowering the yield of propylene. In this way, ZSM-22 with increased mesoporosity has been shown as a promising zeolitic structure.

When used as an additive or used within an FCC catalyst, the mesoporous ZSM-22 of the present invention can be combined with other olefin-selective zeolites and other materials. For example, as part of an FCC catalyst it can be combined with typical Y Zeolite compounds. As another example, when ZSM-22 is combined with ZSM-5 an increase production of propylene is shown than the individual components. Examples of suitable olefin-selective zeolites are MFI-type zeolites, MEL-type zeolites such as ZSM-11, MTW-type zeolites such as ZSM-12, MWW-type zeolites such as MCM-22, MCM-36, MCM-49, MCM-56, and BEA-type zeolites such as zeolite beta. MFI-type zeolites are preferred. MFI-type zeolites are as defined in the ATLAS OF ZEOLITE STRUCTURE TYPES, W. M. Meier and D. H. Olson, 3rd revised edition (1992), Butterworth-Heinemann, and include ZSM-5, ST-5, ZSM-8, ZSM-11, silicalite, LZ-105, LZ-222, LZ-223, LZ-241, LZ-269, L2-242, AMS-1B, AZ-1, BOR-C, Boralite, Encilite, FZ-1, NU-4, NU-5, T5-1, TSZ, TSZ-III, TZ01, TZ, USC-4, USI-108, ZBH, ZB-11, ZBM-30, ZKQ-1B, ZMQ-TB. Further, the mesoporous ZSM-22 can be stabilized with the use of phosphorous compounds as is known in the art. When utilized, the additional zeolites may be added in an amount between about 2 wt % and about 60 wt %

Additives according to this invention can be added to an FCC unit with the hydrocarbon feed, simultaneously with one or more catalysts, or after the hydrocarbon feed and one or more catalysts have been added. In one embodiment, additive according to this invention is combined with one or more FCC catalysts. Said catalyst composition can suitably be used in the catalytic cracking of hydrocarbon feedstocks and has high efficiency in the production of light olefins while maintaining the bottoms conversion. The catalyst composition may also be used in the so-called DCC process even when using lower temperatures than usual in DCC processes.

EXAMPLES

All reactions are done in a typical MAT reactor (fixed bed) at 520° C. with a gas GC attached to analyze gases coming off and a chilled liquid collector which is then analyzed via a GC after the reaction is complete. A varying amount of catalyst is introduced into the reactor for a fixed amount of feed. The feed consists of either an equal weight blend of C5 to C7 olefin or a typical VGO crude feed. The olefin blend is used as the probe molecules since ZSM-5 cracks primarily olefins in the gasoline range to generate LPG gases. A typical FCC catalyst was steamed at 788 C for 20 hours in 100% steam to generate a deactivated FCC catalyst. The ZSM-5 additive is a commercial grade from Albemarle and was used either fresh or steam deactivated as for the FCC catalyst. ZSM-22 was either used fresh or steamed neat, but it was pressed and sieved to generate particles within a distribution typical of catalyst. The additive and ZSM-22 were tested with and without the FCC catalyst with the feed. Products were analyzed by GC and yields were normalized.

The ZSM-22 had varied initial silica to alumina ratio (Si/Al) from 25 to 40 and it was tested as-is and after modification with base/acid to generate mesopores. Initially the ZSM-22 was treated with a basic solution of 0.2 M caustic solution in a liquid to solid ratio of 33:1 at 65° C. for 30 minutes with agitation. After filtering and washing to remove excess sodium (to a pH of 7), the solid was suspended in a solution of oxalic acid (1 g zeolite to 2.5 g oxalic acid in 25.5 g water) at 70° C. for two hours followed by filtration and washing. Samples were calcined at 375° C. for three hours and labeled as mesoporous-ZSM-22. The results of the experiments were included in the below Table 1 and Table 2 as well as FIGS. 1 and 2.

Table 1 shows the selectivity data for the cracking of C5-C6-C7 olefins at 520° C. and 30 sec TOS for meso-ZSM-22 and commercial ZSM-5. For this example, 0.3 g of meso-ZSM-22 and 1 g of commercial ZSM-5 were compared using the above process. The results show clearly that ZSM-22 is more selective towards propylene while yielding less aromatics than a ZSM-5 containing additive.

TABLE 1

Selectivity data for the cracking of C5-C6-C7 olefins at 520° C. and 30 sec TOS for meso-ZSM-22 and Commercial Additive.

| | comparison EXPERIMENT | | | | | |
|---|---|---|---|---|---|---|
| | MESO-ZSM-22 0.30 g | | | Commercial ZSM-5 Additive 1 g | | |
| CATOIL | 0.75 | 1.00 | 1.49 | 0.75 | 1.00 | 1.49 |
| conv | 79.99 | 86.03 | 91.77 | 86.44 | 89.09 | 91.02 |
| tos | 30 | 30 | 30 | 30 | 30 | 30 |
| Olefins | 85.79 | 84.73 | 85.55 | 78.46 | 79.01 | 76.58 |
| AROMATICS | 0.94 | 1.44 | 1.29 | 4.07 | 4.91 | 6.15 |
| NAPHTHENES | 2.23 | 2.33 | 1.55 | 1.62 | 1.78 | 1.47 |
| PARAFFINS | 9.77 | 10.48 | 10.87 | 14.96 | 13.73 | 14.59 |
| COKE1 | 1.27 | 1.02 | 0.74 | 0.89 | 0.56 | 1.21 |
| BALANCE | 100 | 100 | 100 | 100 | 100 | 100 |
| propylene | 24.15 | 26.14 | 28.58 | 23.77 | 24.116 | 25.78 |

With reference to Table 2 and FIG. 2, it is shown the propylene and aromatic selectivity plots for FCC+ commercial ZSM-5 and FCC+ commercial ZSM-5+meso-ZSM-22 for the cracking of C5-C6-C7 olefins at 520° C. and 30 sec TOS. The two samples were compared using the above process. The data shows how a combination of ZSM-22 in a typical FCC+ZSM-5 containing additive will yield higher amounts of propylene with lower amounts of aromatics being generated.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise. This invention is susceptible to considerable variation in its practice. Therefore the foregoing description is not intended to limit, and should not be construed as limiting, the invention to the particular exemplifications presented hereinabove.

What is claimed is:

1. A process for producing propylene from a hydrocarbon feedstock, said process comprising the steps of:
   a. providing an FCC catalyst composition comprising a particulate, said particulate comprising ZSM-22 at an amount in the range of about 15 to about 50 wt %, based upon the weight of the particulate, wherein the the ZSM-22 is treated to increase its mesoporosity;
   b. contacting the FCC catalyst composition with the hydrocarbon feedstock, at one or more temperatures in the range of about 400 to about 650° C., with a dwell time in the range of about 0.5 to about 12 seconds to produce propylene.

2. The process of claim 1 wherein the ZSM-22 is treated to increases its mesoporous volume (cm$^3$/g) by a factor of 1.5.

3. The process of claim 1 wherein the treated ZSM-22 has a mesoporosity of at least 0.075 cm3/g measured as the Vmesopore (cm3/g).

TABLE 2

Selectivity data for the cracking of C5-C6-C7 olefins at 520° C. and 30 sec TOS for the blend of FCC + Commercial ZSM-5 without and with meso-ZSM-22.

| | comparison EXPERIMENT | | | | | |
|---|---|---|---|---|---|---|
| | low REO FCC + 5% commercial ZSM-5 Additive (STM) | | | low REO FCC + 5% commercial ZSM-5 Additive(STM) + meso-ZSM-22 (80/20/5 parts) | | |
| conversion | 82.36 | 82.38 | 84.44 | 84.24 | 84.57 | 85.28 |
| CAT/OIL | 0.37 | 0.50 | 0.75 | 0.75 | 1.00 | 1.49 |
| TOS | 30 | 30 | 30 | 30 | 30 | 30 |
| Olefins | 69.46 | 68.28 | 66.60 | 70.96 | 70.43 | 69.18 |
| AROMATICS | 7.17 | 8.34 | 9.46 | 5.05 | 6.43 | 7.86 |
| NAPHTHENES | 1.14 | 0.98 | 0.67 | 0.68 | 0.72 | 0.52 |
| PARAFFINS | 20.78 | 20.84 | 20.92 | 20.61 | 20.56 | 20.28 |
| COKE1 | 1.46 | 1.55 | 2.35 | 2.70 | 1.86 | 2.15 |
| BALANCE | 100 | 100 | 100 | 100 | 100 | 100 |
| propylene | 24.31 | 25.19 | 25.91 | 25.54 | 26.74 | 27.09 |

80/20/5 parts referrs to 80 parts low RE-FCC, 20 parts ZSM-22, 5 parts Commercial ZSM-5 additive

4. The process of claim 1 wherein the FCC catalyst composition comprises a mixture of at least the particulate comprising said ZSM-22, and at least one second particulate comprising a ZSM-5 zeolite.

5. The process of claim 1 wherein the FCC catalyst composition further comprises ZSM-5 in the same particulate as said ZSM-22.

6. A process as in claim 1 wherein contacting in step b) takes place in a fluidized bed reactor.

\* \* \* \* \*